United States Patent

Seitz et al.

Patent Number: 5,371,267
Date of Patent: Dec. 6, 1994

[54] SUBSTITUTED AMINO ACID AMIDE DERIVATIVES THEIR PREPARATION AND USE

[75] Inventors: Thomas Seitz, Monheim; Wolfgang Bender, Wuppertal; Heinz-Wilhelm Dehne, Monheim, all of Germany

[73] Assignee: Bayer Aktiengesellschaft, Leverkusen, Germany

[21] Appl. No.: 961,998

[22] Filed: Oct. 16, 1992

Related U.S. Application Data

[63] Continuation-in-part of Ser. No. 757,744, Sep. 11, 1991, abandoned.

[30] Foreign Application Priority Data

Sep. 22, 1990 [DE] Germany .................. 4030062

[51] Int. Cl.$^5$ .................. C07C 271/50; A01N 47/18; A01N 47/22
[52] U.S. Cl. .................. 560/27; 546/275; 546/300; 546/335; 560/9; 560/13; 560/21; 560/28
[58] Field of Search .......... 514/332, 335, 351, 357, 514/487, 488, 481; 546/275, 300, 335; 560/9, 13, 21, 27, 28

[56] References Cited

U.S. PATENT DOCUMENTS

| | | | |
|---|---|---|---|
| 4,324,781 | 4/1982 | Okamoto et al. | 514/481 |
| 4,939,170 | 7/1990 | Kruger et al. | 514/483 |
| 5,158,962 | 10/1992 | Seitz et al. | 514/357 |
| 5,210,084 | 5/1993 | Wollweber et al. | 514/237.5 |

FOREIGN PATENT DOCUMENTS

| | | |
|---|---|---|
| 0398072 | 5/1990 | European Pat. Off. |
| 0398072 | 11/1990 | European Pat. Off. |
| 425425 | 7/1991 | European Pat. Off. |
| 873049 | 6/1975 | Germany |
| 47-27011 | 7/1972 | Japan .................. 514/488 |
| 49-16933 | 4/1974 | Japan .................. 514/488 |
| 49-31094 | 8/1974 | Japan .................. 514/488 |

OTHER PUBLICATIONS

Chemical Abstracts, vol. 109, No. 11, Sep. 12, 1988.

*Primary Examiner*—José G. Dees
*Assistant Examiner*—B. Frazier
*Attorney, Agent, or Firm*—Sprung Horn Kramer & Woods

[57] ABSTRACT

Amino acid derivatives of the general formula (I)

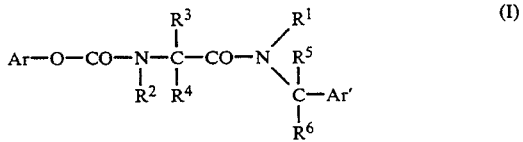

are disclosed. The active compounds are suitable for use as plant protection agents, in particular as fungicides.

13 Claims, No Drawings

SUBSTITUTED AMINO ACID AMIDE DERIVATIVES THEIR PREPARATION AND USE

This is a continuation-in-part of application Ser. No. 757,744, filed Sep. 11, 1991, now abandoned.

The present invention relates to new substituted amino acid amide derivatives and a process for their preparation, as well as their use in pesticides.

The substances according to the invention have an outstanding action in the control of pests. In particular, the substances according to the invention can be employed as fungicides, mainly in plant protection.

Certain amino acid amides have already been disclosed such as, for example, N-tert.-butoxycarbonyl-L-leucylbenzylamide (EP-A-236,874).

However, the use of these compounds in pesticides has not been described.

The present invention therefore relates to new amino acid amide derivatives of the general formula (I)

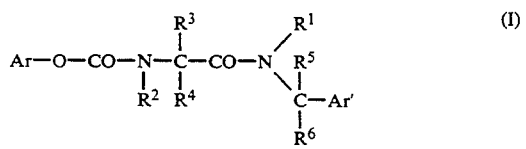

in which

Ar and Ar' are identical or different and represent unsubstituted or substituted aryl, unsubstituted or substituted aralkyl, unsubstituted or substituted heteroaryl and unsubstituted or substituted heteroarylalkyl, $R^1$, $R^2$, $R^4$, $R^5$ and $R^6$ are identical or different and represent hydrogen or alkyl and $R^3$ represents cycloalkyl.

Moreover, the compounds of the formula (I) can contain one or more centres of chirality and can therefore exist in various mixtures of enantiomers and diastereomers which, if appropriate, can be separated by customary methods. The invention claims the pure enantiomers and diastereomers as well as the mixtures.

For the sake of simplicity, the following text will always mention compounds of the formula (I), even though this is understood to mean the pure compounds as well as mixtures containing various proportions of isomeric, enantiomeric and diastereomeric compounds.

Formula (I) provides a general definition of the substituted amino acid amide derivatives according to the invention.

Unless defined otherwise, preferred meanings in the following general formulae are:

Alkyl, individually or in composite radicals
  straight-chain or branched alkyl having 1 to 6, in particular 1 to 4, carbon atoms. The following may be mentioned by way of example and as being preferred: methyl, methyl, n.- and i.-propyl, n-, i-, s- and t-butyl.

Cycloalkyl
  represents a 3- to 7-membered ring, in particular a ring having 3, 5 or 6 carbon atoms. The following may be mentioned by way of example and as being preferred: cyclopropyl, cyclobutyl, cyclopentyl, cyclohexyl and cycloheptyl.

Aryl
  unsubstituted or substituted aryl having 6 to 10 carbon atoms. The following may be mentioned by way of example and as being preferred: in each case unsubstituted or substituted phenyl and naphthyl, in particular unsubstituted or substituted phenyl.

Aralkyl
  unsubstituted or substituted aralkyl having 1 to 4, in particular 1 or 2, carbon atoms in the straight-chain or branched alkyl moiety and 6 to 10 carbon atoms, preferably phenyl or naphthyl in the aryl moiety. The following may be mentioned by way of example and as being preferred: benzyl, 1,1- and 1,2-phenethyl and 1,1-, 1,2-, 1,3- and 2,2-phenylpropyl.

Heteroaryl
  unsubstituted or substituted 5- to 9-membered ring, in particular 5- to 7-membered ring, which contains 1 to 4, preferably 1 to 3, identical or different hetero atoms. Preferred hetero atoms which may be mentioned are oxygen, sulphur and nitrogen. The following may be mentioned by way of example and as being preferred: pyrimidinyl, pyrrolyl, isothiazolyl, oxazolyl, thienyl, furyl, pyridazinyl, pyrazinyl, isooxazolyl, thiazolyl and, in particular, pyridyl.

Heteroarylalkyl
  the heteroaryl moiety corresponds to the above-mentioned definitions and preferred series. The alkyl moiety is straight-chain or branched and contains 1 to 4, in particular 1 or 2, carbon atoms. The following may be mentioned by way of example and as being preferred: heteroarylmethyl, 1,1- and 1,2-heteroarylethyl and 1,1-, 1,2-, 1,3- and 2,2-heteroarylpropyl.

The optionally substituted radicals of the general formulae can carry one or more, preferably 1 to 3, in particular 1 or 2, identical or different substituents. The following substituents may be mentioned by way of example and as being preferred: alkyl having preferably 1 to 4, in particular 1 or 2, carbon atoms such as methyl, ethyl, n.- and i.-propyl and n.-, i.-, sec.- and t.-butyl; alkoxy having preferably 1 to 4, in particular 1 or 2, carbon atoms such as methoxy, ethoxy, n.- and i.-propyloxy and n.-, i.-, sec.- and t.-butyloxy; alkylthio having preferably 1 to 4, in particular 1 or 2, carbon atoms such as methylthio, ethylthio, n.- and i.-propylthio and n.-, i.-, sec.- and t.-butylthio; halogenoalkyl, halogenoalkoxy and halogenoalkylthio, each of which has preferably 1 to 4, in particular 1 or 2, carbon atoms and preferably 1 to 9, in particular 1 to 5, halogen atoms, the halogen atoms being identical or different and preferably representing fluorine, chlorine or bromine, in particular fluorine, such as trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; hydroxyl; halogen, preferably fluorine, chlorine, bromine and iodine, in particular fluorine, chlorine and bromine; cyano; nitro; dialkylamino having preferably 1 to 4, in particular 1 or 2, carbon atoms per alkyl group such as dimethylamino and diethylamino; carboxyl; alkylalkoxy having 1 to 4, in particular 1 or 2, carbon atoms in each alkyl moiety; carbonylalkoxy having 1 to 4, in particular 1 or 2, carbon atoms in the alkyl moiety such as carbonylmethoxy and carbonyl ethoxy; carbonylalkyl having 1 to 4, in particular 1 or 2, carbon atoms in the alkyl moiety such as acetyl and propionyl; formyl; carbonylaryloxy having 5 to 10 carbon atoms in the aryl moiety such as carbonylphenoxy; carbonylaryl having 6 to 10 carbon atoms in the aryl moiety such as benzoyl; oxycarbonylalkyl having 1 to 4, in particular 1 or 2, carbon atoms in the alkyl moiety such as acetoxy; oxycarbonylaryl having 6 to 10 carbon atoms in the aryl moiety such as benzoyloxy; carboxylamino, carbonylaminoalkyl, carbonylaminodialkyl, aminocarbonyl, alkylaminocarbonyl, aminocarbonylalkyl and alkylaminocarbonylalkyl, each of which has 1 to 4, in particular 1 or 2, carbon atoms in the alkyl moiety; sulphonamido; sulphonalkyl; sulphonylalkyl and sulphonylalkoxy, each of which has 1 to 4, in particular 1 or 2, carbon atoms; phenyl or phenoxy, each of which is unsubstituted or substituted by halogen, in particular fluorine, chlorine and/or bromine.

The definitions mentioned here also apply analogously to the definitions in the following preferred combinations of radicals.

Preferred compounds of the formula (I) are those in which $R^1$, $R^2$, $R^4$, $R^5$ and $R^6$ are identical or different and represent hydrogen or straight-chain or branched alkyl having 1 to 4 carbon atoms, $R^3$ represents a cycloalkyl ring having 3 to 7 carbon atoms and Ar and Ar' are identical or different and represent in each case unsubstituted or substituted phenyl and pyridyl or phenylalkyl which has 1 to 4 carbon atoms in the straight-chain or branched alkyl moiety and which is unsubstituted or substituted in the phenyl moiety, suitable substituents in the pyridyl or phenyl moiety in each case being: alkyl, alkoxy and alkylthio, each of which has 1 to 4 carbon atoms; halogenoalkyl, halogenoalkoxy and halogenoalkylthio, each of which has 1 to 4 carbon atoms and 1 to 9 halogen atoms, the halogen atoms being identical or different; hydroxyl; halogen; cyano; nitro; dialkylamino having 1 to 4 carbon atoms per alkyl group; carboxyl, alkylalkoxy having 1 to 4 carbon atoms in each alkyl moiety; carbonylalkoxy having 1 to 4 carbon atoms in the alkyl moiety; carbonylalkyl having 1 to 4 carbon atoms in alkyl moiety; formyl; carbonylaryloxy having 5 to 10 carbon atoms in the aryl moiety; carbonylaryl having 6 to 10 carbon atoms in the aryl moiety; oxycarbonylalkyl having 1 to 4 carbon atoms in the alkyl moiety; oxycarbonylaryl having 6 to 10 carbon atoms in the aryl moiety; carbonylamino, carbonylaminoalkyl, carbonylaminodialkyl, aminocarbonyl, alkylaminocarbonyl, aminocarbonylalkyl and alkylaminocarbonylalkyl, each of which has 1 to 4 carbon atoms in the alkyl moiety; sulphonamido; sulphonalkyl; sulphonylalkyl and sulphonylalkoxy, each of which has 1 to 4 carbon atoms; and phenyl or phenoxy, each of which is unsubstituted or substituted by halogen.

Particularly preferred compounds of the formula (I) are those in which $R^1$ and $R^2$ represent hydrogen, $R^3$ represents a cycloalkyl ring having 3 to 6 carbon atoms, $R^4$, $R^5$ and $R^6$ are identical or different and represent hydrogen, methyl or ethyl, Ar represents phenyl which is unsubstituted or monosubstituted to trisubstituted by identical or different substituents, suitable substituents being the following: alkyl, alkoxy and alkylthio, each of which has 1 or 2 carbon atoms; halogenoalkyl, halogenoalkoxy and halogenoalkylthio, each of which has 1 or 2 carbon atoms and 1 to 5 halogen atoms, the halogen atoms being identical of different; hydroxyl, fluorine, chlorine, bromine and iodine; cyano; nitro; dialkylamino having 1 or 2 carbon atoms per alkyl group; carboxyl; alkylalkoxy having 1 or 2 carbon atoms in each alkyl moiety; carbonylalkoxy having 1 or 2 carbon atoms in the alkyl moiety; carbonylalkyl having 1 or 2 carbon atoms in the alkyl moiety; formyl; carbonylphenoxy; benzoyl; oxycarbonylalkyl having 1 or 2 carbon atoms; benzoyloxy; carbonylamino, carbonylaminoalkyl, carbonylaminodialkyl, aminocarbonyl, alkylaminocarbonyl, aminocarbonylalkyl and alkylaminocarbonylalkyl, each of which has 1 or 2 carbon atoms in the alkyl moiety; sulphonamido; sulphonalkyl, sulphonylalkyl and sulphonylalkoxy, each of which has 1 or 2 carbon atoms; or phenyl or phenoxy, each of which is unsubstituted or substituted by fluorine, chlorine or bromine and, Ar' represents phenyl or pyridyl, each of which is unsubstituted or monosubstituted to trisubstituted by identical or different substituents, or represents phenylalkyl which has 1 or 2 carbon atoms in the alkyl moiety and which is unsubstituted or monosubstituted to trisubstituted in the phenyl moiety, phenyl substituents in each case being the phenyl substituents mentioned above.

Very particularly preferred compounds of the formula (I) are those in which $R^1$ represents hydrogen, $R^2$ represents hydrogen, $R^4$ represents hydrogen, $R^3$ represents a cyclopropyl, cyclopentyl or cyclohexyl ring, $R^5$ represents hydrogen or methyl, $R^6$ represents hydrogen, methyl or ethyl, Ar represents phenyl which is unsubstituted or monosubstituted to disubstituted by identical or different substituents, suitable substituents being the following: methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine, fluorine, nitro and cyano and Ar' represents benzyl or 1,2-phenethyl, each of which is unsubstituted or monosubstituted to disubstituted in the phenyl moiety by identical or different substituents, but in particular represents phenyl which is unsubstituted or monosubstituted to disubstituted by identical or different substituents, suitable phenyl substituents in each case being the phenyl substituents mentioned above.

The substituted amino acid amide derivatives of the general formula (I)

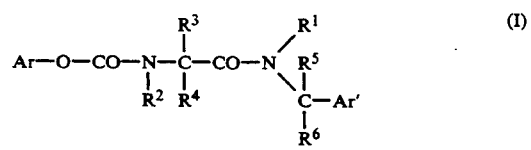

in which $R^1$, $R^2$, $R^3$, $R^4$, $R^5$, $R^6$, Ar and Ar' have the abovementioned meaning are obtained when a substituted amino acid of the formula (II)

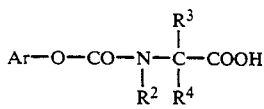 (II)

in which

Ar, $R^2$, $R^3$ and $R^4$ have the abovementioned meaning, or their carboxyl-activated derivatives,
are reacted with an amine of the formula (III)

$$HNR^1—CR^5R^6Ar'  \quad (III)$$

in which

Ar', $R^1$, $R^5$ and $R^6$ have the abovementioned meaning,
if appropriate in the presence of a catalyst, if appropriate in the presence of an acid-binding agent and if appropriate in the presence of a diluent.

If, for example, phenoxycarbonyl-cyclohexyl-glycine and 4-chlorophenethylamine are used as starting materials, the course of the process according to the invention can be illustrated by the following equation:

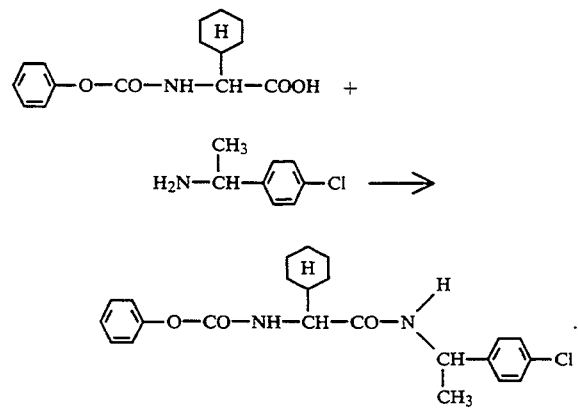

Formula (II) provides a general definition of the amino acid derivatives to be used as starting substances for carrying out the process according to the invention. In this formula, Ar, $R^2$, $R^3$ and $R^4$ preferably have the meanings which have already been mentioned in connection with the description of the substances of the formula (I) according to the invention as being preferred for these substituents.

The substituted amino acid derivatives of the formula (II) or their carboxyl-activated derivatives

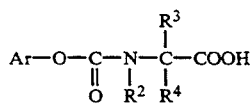 (II)

in which

Ar represents unsubstituted or substituted aryl, unsubstituted or substituted aralkyl, unsubstituted or substituted heteroaryl and unsubstituted or substituted heteroarylalkyl $R^2$ and $R^4$ are identical or different and represent hydrogen or alkyl and $R^3$ represents cycloalkyl are new with the exception of the compounds N-benzyl α-(carbonylamino)cyclohexaneacetate (compare GB 873,049); 4-nitrophenyl α-[[(phenylmethoxy)carbonyl-]amino]-(S)-cyclohexaneacetate (compare EP 19,589); 4-nitrophenyl α-[[(phenylmethoxy)carbonyl]amino]-(R)-cyclohexaneacetate (compare EP 34,122); α-[[(phenylmethoxy)carbonyl]amino]-(R)-cyclohexaneacetic acid α-[[(phenylmethoxy)carbonyl]-amino]-(S)-cyclohexaneacetic acid (compare, inter alia, Hoppe-Seyler's Z. Physiol. Chem., 359 (8), 897–916, 1978) and N-benzyl α-(carboxyamino)-(L)-cyclohexaneacetate (compare J. Med. Chem., 12 (5), 737–740, 1969).

The new substituted amino acid derivatives of the formula (II) or their carboxyl-activated esters can be obtained analogously to known processes, by reacting, for example, amino acid derivatives of the formula (IV)

 (IV)

in which $R^2$, $R^3$ and $R^4$ have the abovementioned meaning
with acid chlorides of the formula (V)

 (V)

in which

Ar has the abovementioned meaning,
if appropriate in the presence of an acid-binding agent such as, for example, sodium hydroxide solution or pyridine, and if appropriate in the presence of a diluent such as, for example, dichloromethane, at temperatures from −10° C. to +10° C. (compare, inter alia, Tetrahedron Lett. 30 (39), 5227–5230, 1989 and J. Med. Chem., 12 (5), 737–740, 1969).

Formula (IV) provides a general definition of the amino acid derivatives of the formula (IV) required as starting substances for the preparation of the substituted amino acid derivatives of the formula (II). In this formula (IV), $R^2$, $R^3$ and $R^4$ represent those radicals which have already been mentioned for these substituents in connection with the description of the compound of the formula (I) according to the invention.

The amino acid derivatives of the formula (IV) are generally known compounds of organic chemistry.

In the acid chlorides of the formula (V) which are furthermore required as starting substances for the preparation of the substituted amino acid derivatives of the formula (II), Ar has the meaning which has already been mentioned in connection with the description of the compound of the formula (I) according to the invention. The acid chlorides of the formula (V) are also generally known compounds of organic chemistry.

Suitable carboxyl-activated derivatives of the amino acids of the formula (II) are all carboxyl-activated derivatives such as acid halides such as, for example, acid chlorides, acid azides, furthermore symmetric and mixed anhydrides such as, for example, the mixed O-alkylcarbonic anhydrides, furthermore activated esters such as, for example, p-nitrophenyl esters or N-hydroxysuccinimide esters, as well as activated forms of the amino acids which have been prepared in situ with condensing agents such as, for example, dicyclohexylcarbodiimide or carbonyldiimidazole.

It is preferred to employ the acid chlorides and mixed anhydrides which correspond to the amino acids of the formula (II). They can be prepared by reacting the amino acids of the formula (II) or their salts with a halogenating agent or one of the generally known agents for the preparation of mixed anhydrides such as, for example, phosphorus pentachloride, thionyl chloride, oxalyl chloride or isobutyl chloroformate, in the generally known fashion. The use of isobutyl chloroformate is preferred.

The reaction can be carried out in the presence of indifferent diluents such as, for example, aromatic, non-aromatic or halogenated hydrocarbons such as: ketones, such as, for example, acetone; esters, such as, for example, ethyl acetate; amides, such as, for example, dimethylformamide-; nitriles such as, for example, acetonitrile; chlorohydrocarbons such as, for example, methylene chloride; hydrocarbons such as, for example, toluene; or ethers such as, for example, tetrahydrofuran, or their mixtures, and/or in the presence of an acid-binding agent such as, preferably, a tertiary amine such as, for example, triethylamine, pyridine or N-methylpiperidine, at temperatures from −78° C. to 100° C., preferably −60° C. to 25° C.

Formula (III) provides a general definition of the amines furthermore to be used as starting substances for carrying out the process according to the invention. In these formulae, $R^1$, Ar', $R^5$ and $R^6$ have the abovementioned meanings.

The amines of the formula (III) are generally known compounds of organic chemistry.

Suitable diluents for the process according to the invention are inert organic solvents such as: ketones such as acetone or ethyl methyl ketone; esters such as ethyl acetate or methyl acetate; amides such as dimethylformamide; nitriles such as acetonitrile; chlorohydrocarbons such as methylene chloride or carbon tetrachloride; hydrocarbons such as toluene, or ethers such as tetrahydrofuran and, if appropriate, water and mixtures of these substances.

Suitable acid-binding agents for the process according to the invention are customary inorganic and organic acid binders. These preferably include tertiary amines such as triethylamine, pyridine or N-methylpiperidine, and also inorganic bases, for example metal hydroxides such as sodium hydroxide and potassium hydroxide, or metal carbonates such as sodium carbonate or calcium carbonate.

If appropriate, the process according to the invention is carried out in the presence of a catalyst. Examples which may be mentioned are 4-dimethylaminopyridine, 1-hydroxybenzotriazole or dimethylformamide.

When carrying out the process, the temperatures can be varied within a substantial range. In general, the process is carried out at −78° to +120° C., preferably at −60° to +40° C.

When carrying out the process according to the invention, equimolar amounts are preferably used.

The amino acid derivatives of the formula (II) are employed in the process as pure optical isomers (D or L form) or as racemates.

The invention embraces the pure isomers as well as the mixtures. These mixtures can be separated into the components by customary methods, for example selective crystallisation from suitable solvents or chromatography on silica gel or aluminium oxide. Racemates can be resolved by customary methods to give the individual enantiomers, for example by salt formation with optically active acids such as champhersulphonic acid or dibenzoyltartaric acid and selective crystallisation, or by the formation of derivatives with suitable optically active reagents, resolution of the diastereomeric derivatives and back-conversion, or resolution on optically active column material.

The active compounds of the formula (I) according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success protectively for combating Phytophthora species on tomatoes.

Depending on their particular physical and/or chemical properties, the active compounds can be converted to the customary formulations, such as solutions, emulsions, suspensions, powders, foams, pastes, granules, aerosols, very fine encapsulations in polymeric substances and in coating compositions for seeds, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogeno hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in the formulations as a mixture with other known active compounds such as fungicides, insecticides, acaricides and herbicides, and as mixtures with fertilisers and growth regulators.

The active compounds can be applied as such or in the form of the formulations or the use forms prepared therefrom, such as ready-to-use solutions, suspensions, wettable powders, pastes, soluble powders, dusts and granules. They are applied in the customary manner, for example by watering, spraying, atomising, scattering, dusting, foaming, brushing on and the like. It is furthermore possible to apply the active compounds by the ultra-low-volume method or to inject the active compound preparation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seeds, amounts of active compound of 0.001 to 50 g per kilogram of seed, preferably 0.01 to 10 g are generally required.

In the treatment of the soil, active compound concentrations of 0.00001 to 0.1% by weight, preferably 0.0001 to 0.02%, are required at the place of action.

PREPARATION EXAMPLES

Example 1

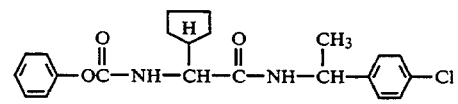

1.47 g (6 mmol) of phenoxycarbonyl-L-cyclopentylglycine are dissolved in 50 ml of $CH_2Cl_2$ and the solution is treated with 0.59 g (6 mmol) of N-methylpiperidine at $-20°$ C. After the mixture has been stirred for 5 minutes at $-20°$ C., 0.82 g (6 mmol) of isobutyl chloroformate are added dropwise, stirring is continued for 10 minutes at $-20°$ C., the mixture is cooled to $-60°$ C., and 0.93 g (6 mmol) of 1-(4-chlorophenyl)ethylamine, dissolved in 5 ml of $CH_2Cl_2$, are added. Stirring is continued for 2 hours at $-15°$ C. and then for a further 15 hours at room temperature. For working up, solids are filtered off, the solution is concentrated in vacuo, and the residue is taken up in $CH_2Cl_2$. The organic phase is washed in succession with water, $NaHCO_3$ solution and water, dried over $Na_2SO_4$ and freed from solvent in vacuo. 1.05 g (44% of theory) of colorless $N^2$-phenoxycarbonyl-$N^1$[rac.-1-(4-chlorophenyl)ethyl]-L-cyclopentylglycine of melting point 167° C. are obtained.

The following compounds of the formula (I) are obtained analogously to Example 1:

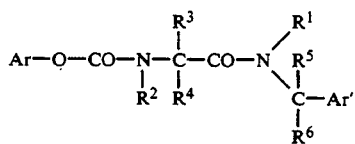

TABLE 1

| Example No. | Ar | R¹ | R² | R³ | R⁴ | R⁵ | R⁶ | Ar' | Physical Constant |
|---|---|---|---|---|---|---|---|---|---|
| 2 | phenyl | H | H | cyclopentyl | H | H | CH₃ | 4-methylphenyl | m.p. 160° C. racemic amide of the L-amino acid |
| 3 | phenyl | H | H | cyclopentyl | H | H | CH₃ | 4-methoxyphenyl | m.p. 146° C. racemic amide of the L-amino acid |
| 4 | phenyl | H | H | cyclopentyl | H | H | CH₃ | 4-chlorophenyl | m.p. 187° C. (R+) amide of the L-amino acid |

EXAMPLE A

Phytophthora test (tomato)/protective
Solvent: 4.7 parts by weight of acetone
Emulsifier: 0.3 parts by weight of alkyl-aryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. When the spray coating has dried on, the plants are inoculated with an aqueous spore suspension of *phytophthora infestans*.

The plants are placed in an incubation cabin at 100% relative atmospheric humidity at approx. 20° C.

Evaluation takes place 3 days after inoculation.

An excellent fungicidal activity is shown by the compounds of Preparation Examples (1), (2), (3) and (4).

It will be appreciated that the instant specification and claims are set forth by way of illustration and not limitation, and that various modifications and changes may be made without departing from the spirit and scope of the present invention.

What is claimed is:

1. An amino acid amide derivative of the formula

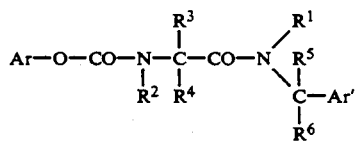

(I)

$R^1$, $R^2$, $R^4$, $R^5$ and $R^6$ are identical or different and represent hydrogen or straight-chain or branched alkyl having 1 to 4 carbon atoms, $R^3$ represents a cycloalkyl ring having 3 to 7 carbon atoms and Ar and Ar' are identical or different and represent in each case unsubstituted or substituted phenyl, naphthyl, pyridyl, or phenylalkyl or naphthylalkyl which has 1 to 4 carbon atoms in the straight-chain or branched alkyl moiety and which is unsubstituted or substituted on the phenyl or naphthyl moiety, substitutents on the pyridyl, phenyl or naphthyl moiety when present being selected from the group consisting of alkyl, alkoxy and alkylthio, each of which has 1 to 4 carbon atoms; halogenoalkyl, halogenoalkoxy and halogenoalkylthio, each of which has 1 to 4 carbon atoms and 1 to 9 halogen atoms, the halogen atoms being identical or different; hydroxyl; halogen; cyano; nitro; dialkylamino having 1 to 4 carbon atoms per alkyl group; carboxyl, alkylalkoxy having 1 to 4 carbon atoms in each alkyl moiety; carbonylalkoxy having 1 to 4 carbon atoms in the alkyl moiety; carbonylalkyl having 1 to 4 carbon atoms in the alkyl moiety; formyl; carbonylaryloxy having 6 to 10 carbon atoms in the aryl moiety; carbonylaryl having 6 to 10 carbon atoms in the aryl moiety; oxycarbonylalkyl having 1 to 4 carbon atoms in the alkyl moiety; oxycarbonylaryl having 6 to 10 carbon atoms in the aryl moiety; carbonylamino; carbonylaminoalkyl, carbonylaminodialkyl, aminocarbonyl, alkylaminocarbonyl, aminocarbonylalkyl and alkylaminocarbonylalkyl, each of which has 1 to 4 carbon atoms in the alkyl moiety; sulphonamido; sulphonalkyl; sulphonylalkyl and sulphonylalkoxy, each of which has 1 to 4 carbon atoms; and phenyl or phenoxy, each of which is unsubstituted or substituted by halogen.

2. A compound according to claim 1, in which
$R^1$ and $R^2$ represent hydrogen,
$R^3$ represents a cycloalkyl ring having 3 to 6 carbon atoms,
$R^4$, $R^5$ and $R^6$ are identical or different and represent hydrogen, methyl or ethyl,
Ar represents phenyl or naphthyl which is unsubstituted or monosubstituted to trisubstituted by identical or different substitutents selected from the group consisting of alkyl, alkoxy and alkylthio, each of which has 1 or 2 carbon atoms; halogenalkyl, halogenoalkoxy and halogenoalkylthio, each of which has 1 or 2 carbon atoms and 1 to 5 halogen atoms, the halogen atoms being identical or different; hydroxyl, fluorine, chlorine, bromine and iodine, cyano; nitro; dialkylamino having 1 or 2 carbon atoms per alkyl group; carboxyl; alkylalkoxy having 1 or 2 carbon atoms in each alkyl moiety; carbonylalkoxy having 1 or 2 carbon atoms in the alkyl moiety; carbonylalkyl having 1 or 2 carbon atoms in the alkyl moiety; formyl; carbonylphenoxy; benzoyl; oxycarbonylalkyl having 1 or 2 carbon atoms; benzoyloxy; carbonylamino, carbonylaminoalkyl, carbonylaminodialkyl, aminocarbonyl, alkylaminocarbonyl, aminocarbonylalkyl and alkylaminocarbonylalkyl, each of which has 1 or 2 carbon atoms in the alkyl moiety; sulphonamido; sulphonalkyl, sulphonylalkyl and sulphonylalkoxy, each of which has 1 or 2 carbon atoms; or phenyl or phenoxy, each of which is unsubstituted or substituted by fluorine, chlorine or bromine and, Ar' represents phenyl, naphthyl or pyridyl, each of which is unsubstituted or monosubstituted to trisubstituted by identical or different substitutents, or represents phenylalkyl or naphthylalkyl which has 1 or 2 carbon atoms in the alkyl moiety and which is unsubstituted or monosubstituted to trisubstituted in the phenyl or naphthyl moiety, the substituents when present in each case being the phenyl or naphthyl substitutents mentioned above.

3. A compound according to claim 1, in which
$R^1$ represents hydrogen,
$R^2$ represents hydrogen,
$R^4$ represents hydrogen,
$R^5$ represents a cyclopropyl, cyclopentyl or cyclohexyl ring,
$R^6$ represents hydrogen, methyl or ethyl,
Ar represents phenyl or naphthyl which is unsubstituted or monosubstituted to disubstituted by identical or different substitutents selected from the group consisting of methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio, chlorine, bromine, fluorine, nitro and cyano and Ar' represents benzyl or 1,2-phenethyl, each of which is unsubstituted or monosubstituted to disubstituted in the phenyl moiety by identical or different substitutents, the substituents when present being the phenyl or naphthyl substitutents mentioned above.

4. A compound according to claim 1, wherein such compound is $N^2$-phenoxycarbonyl-$N^1$[1-(4-chlorophenyl)ethyl]-L-cyclopentylglycine of the formula

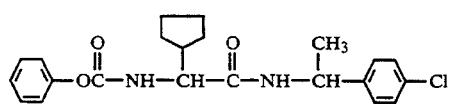

5. A compound according to claim 1, wherein such compound is $N^2$-phenoxycarbonyl-$N^1$[1-(4-methylphenyl)ethyl]-L-cyclopentylglycine of the formula

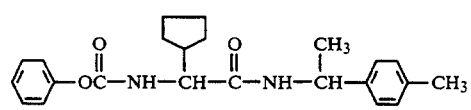

6. A compound according to claim 1, wherein such compound is $N^2$-phenoxycarbonyl-$N^1$[1-(4-methoxyphenyl)ethyl]-L-cyclopentylglycine of the formula

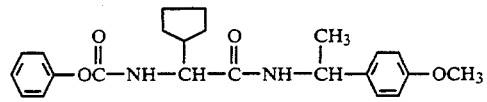

7. A compound according to claim 1, wherein such compound is $N^2$-(2-naphthoxycarbonyl) -$N^1$-[1-(4-chlorophenyl)ethyl]-L-cyclopentylglycine of the formula

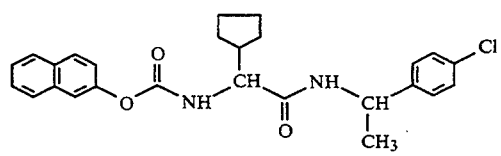

8. A compound according to claim 1, wherein such compound is $N^2$-(2-naphthoxycarbonyl)-$N^1$-[1-(4-methylphenyl)ethyl]-L-cyclopentylglycine of the formula

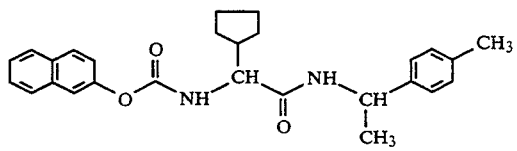

9. A compound according to claim 1, wherein such compound is $N^2$-(1-naphthoxycarbonyl)-$N^1$-[1-(4-ethylphenyl)ethyl]-L-cyclopentylglycine of the formula

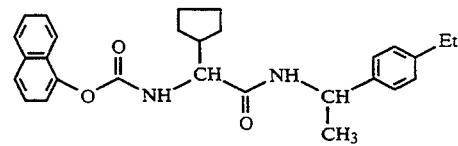

10. A compound according to claim 1, wherein such compound is $N^2$-(1-naphthoxycarbonyl)-$N^1$-[1-(4-methoxyphenyl)ethyl]-L-cyclopentylglycine of the formula

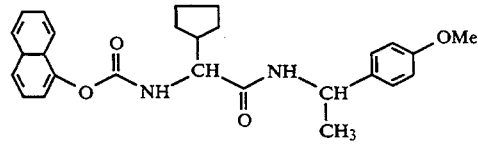

11. A fungicidal composition comprising a fungicidally effective amount of a compound according to claim 1 and a diluent.

12. A method of combating fungi which comprises applying to such fungi or to a fungus habitat a fungicidally effective amount of a compound according to claim 1 and a diluent.

13. The method according to claim 12, wherein such compound is $N^2$-phenoxycarbonyl-$N^1$-[1-(4-chlorophenyl)ethyl]-L-cyclopentylglycine $N^2$-phenoxycarbonyl-$N^1$-[1-(4-methylphenyl)ethyl]-L-cyclopentylglycine $N^2$-phenoxycarbonyl-$N^1$-[1-(4-methoxyphenyl)ethyl]-L-cyclopentylglycine $N^2$-(2-naphthoxycarbonyl)-$N^1$-[1-(4-chlorophenyl)ethyl]-L-cyclopentylglycine $N^2$-(2-naphthoxycarbonyl)-$N^1$-[1-(4-methylphenyl)ethyl]-L-cyclopentylglycine $N^2$-(1-naphthoxycarbonyl)-$N^1$-[1-(4-ethylphenyl)ethyl]-L-cyclopentylglycine $N^2$-(1-naphthoxycarbonyl)-$N^1$-[1-(4-methoxyphenyl)ethyl]-L-cyclopentylglycine

* * * * *

UNITED STATES PATENT AND TRADEMARK OFFICE
CERTIFICATE OF CORRECTION

PATENT NO. : 5,371,267
DATED : December 6, 1994
INVENTOR(S) : Seitz, et al.

It is certified that error appears in the above-indentified patent and that said Letters Patent is hereby corrected as shown below:

Col. 14, line 55   Delete formula and substitute

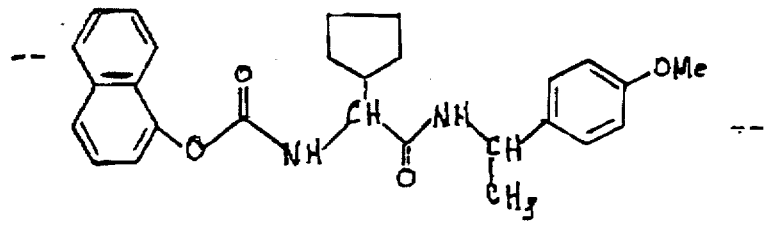

Signed and Sealed this

Second Day of February, 1999

Attest:

Attesting Officer

*Acting Commissioner of Patents and Trademarks*